(12) United States Patent
Valiga et al.

(10) Patent No.: US 6,522,713 B1
(45) Date of Patent: Feb. 18, 2003

(54) IN-ROOM START SCAN SEQUENCE CONTROL AND METHOD OF IMAGING USING SAME

(75) Inventors: Richard A. Valiga, Waukesha, WI (US); Fazle Ali, Brookfield, WI (US); Holly A. McDaniel, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/682,415

(22) Filed: Aug. 30, 2001

(51) Int. Cl.[7] .............................................. G01N 23/00
(52) U.S. Cl. ............................................................ 378/4
(58) Field of Search ........................................ 378/4–20

(56) References Cited

U.S. PATENT DOCUMENTS

| | | | | |
|---|---|---|---|---|
| 5,018,178 A | * | 5/1991 | Katsumata | ...................... 378/4 |
| 5,848,126 A | * | 12/1998 | Fujita et al. | ...................... 378/4 |
| 6,173,031 B1 | * | 1/2001 | Hoffman | ........................ 378/19 |

* cited by examiner

*Primary Examiner*—Craig E. Church
(74) *Attorney, Agent, or Firm*—Ziolkowski Patent Solutions Group, LLC; Michael A. Della Penna; Carl B. Horton

(57) ABSTRACT

An apparatus and method that allows an operator to initiate a prep delay sequence from an area adjacent a patient table are provided for use with x-ray emitting scanners. An operator is allowed to maintain continued focus on a patient to be scanned and closely monitor the patient during the injection sequence. Overall scan time is reduced by decreasing the number of times the operator must travel between the operator console and the patient table. Risk to prolonged radiation exposure is thereby reduced. Ultimately, the present invention allows for better quality patient care, faster scan times and overall increased throughput, reduced repetitive tasks for the operators, reduced risk of x-ray exposure to operators, and, in some circumstances, eliminating the need for multiple operators.

35 Claims, 3 Drawing Sheets

IN-ROOM START SCAN SEQUENCE CONTROL AND METHOD OF IMAGING USING SAME

BACKGROUND OF THE INVENTION

The present invention relates generally to medical imaging and, more particularly, to a method and apparatus of medical imaging using an in-room start scan sequence control.

For typical medical imaging environments employing radiation, such as x-ray and CT, the medical imaging scanner is positioned in one room while an operating console is positioned in another room. Positioning of the operating console in another room helps in limiting an operator or technologist's exposure to radiation. As is well known, prolonged exposure to radiation should be avoided. Therefore, most imaging environments place the operating console in a separate room from the scanner so that during the scanning process, the scanner operator may be a sufficient distance from the scanner and the high frequency electromagnetic energy.

With these known systems, the operator, after preparing the scanning subject, i.e., medical patient, must walk from the patient table to the operator console positioned in a separate room to initiate the scan sequence. At the operator console, the operator initiates the scan sequence by depressing a start button which causes an injector to administer a contrast agent. Typically, there is a delay of approximately 20 to 40 seconds before the x-rays are emitted after the scan button is activated. This 20 to 40 second delay allows the contrast to circulate through the patient's body to the region being scanned. Also during this delay period, the technologist typically walks back to the patient to monitor the patient's reaction to the contrast agent and to ensure that the IV line used to inject the contrast agent is satisfactory. To avoid exposure to radiation, it is imperative that the operator leave the patient and retire to the room housing the operator console before the x-rays are initiated. Typically, there are no timers or indicators to display the elapsed time during this delay sequence thereby requiring the operator to mentally estimate the delay time. As a result, the operator must not only concentrate on the patient, but also remain carefully cognizant of the delay time to avoid potential radiation exposure.

Therefore, it would be desirable to design a system having a set of controls that allows an operator to start a scan sequence directly from the scanner. It would be further desirable to continually display the elapsed time from the start of the scan sequence and before the emission of x-rays so that the operator may easily monitor and be aware of the onset of x-ray emissions. It would further be desirable to enable the operator to initiate the scanning process from an area generally adjacent the patient table.

SUMMARY OF THE INVENTION

The present invention is directed to a method and apparatus of medical imaging overcoming the aforementioned drawbacks. The present invention allows an operator to maintain continued focus on a patient to be scanned and closely monitor the patient during the injection sequence. The present invention reduces overall scan time by reducing the number of times the operator must travel between the operator console and the patient table. Further, an operator's risk to prolonged radiation exposure is also reduced. Ultimately, the present invention allows for better quality patient care, faster scan times and overall increased throughput, reduced repetitive tasks for the operators, reduced risk of x-ray exposure to operators, and, in some circumstances, reducing the need for multiple operators.

Therefore, in accordance with one aspect of the present invention, a gantry control panel for use with a radiation emitting medical imaging scanner is provided. The gantry control panel includes a scan sequence initiator control and a scan sequence terminator control. Further, the gantry control panel is located on a gantry of the radiation emitting medical imaging scanner and is further configured to be non-remotely located from a patient table.

In accordance with another aspect of the present invention, a gantry for use with a radiation emitting medical imaging scanner includes a radiation emitting source, a radiation detector, and an opening for receiving a subject therethrough. The gantry further includes at least one faceplate wherein the at least one faceplate has a first set of controls and a second set of controls. Additionally, one of the first set and the second set of controls is configured to at least initiate a scan sequence.

In accordance with yet another aspect of the present invention, a CT system comprises a radiation projection source, a radiation detector, and a light detector coupled to the radiation detector. A data acquisition system is also provided and is electrically connected to the light detector. The CT system further includes a rotatable gantry positioned about a subject table and having an opening to receive a subject to be scanned therethrough. The gantry includes a set of scanning controls located immediately adjacent the rotatable gantry such that an operator may utilize the controls while near the subject.

In accordance with another aspect of the present invention, a set of gantry controls includes a means for positioning a subject within an imaging space and a means for initiating a scan sequence from an area immediately adjacent the subject. A means for acquiring imaging data is also provided.

In accordance with yet another aspect of the present invention, a method of imaging a subject includes preparing a subject for scanning and positioning the subject within an imaging space. The method further includes initiating a scan process from a set of controls positioned on a side of a gantry and monitoring the subject non-remotely from the set of controls and the subject. The method also includes the step of acquiring imaging data.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those of ordinary skill in the art that the present invention is equally applicable for use with single-slice or other multi-slice configurations. Moreover, the present invention will be described with respect to the detection and conversion of x-rays. However, one of ordinary skill in the art will further appreciate, that the present invention is equally applicable for the detection and conversion of other high frequency electromagnetic energy.

Figure 1:
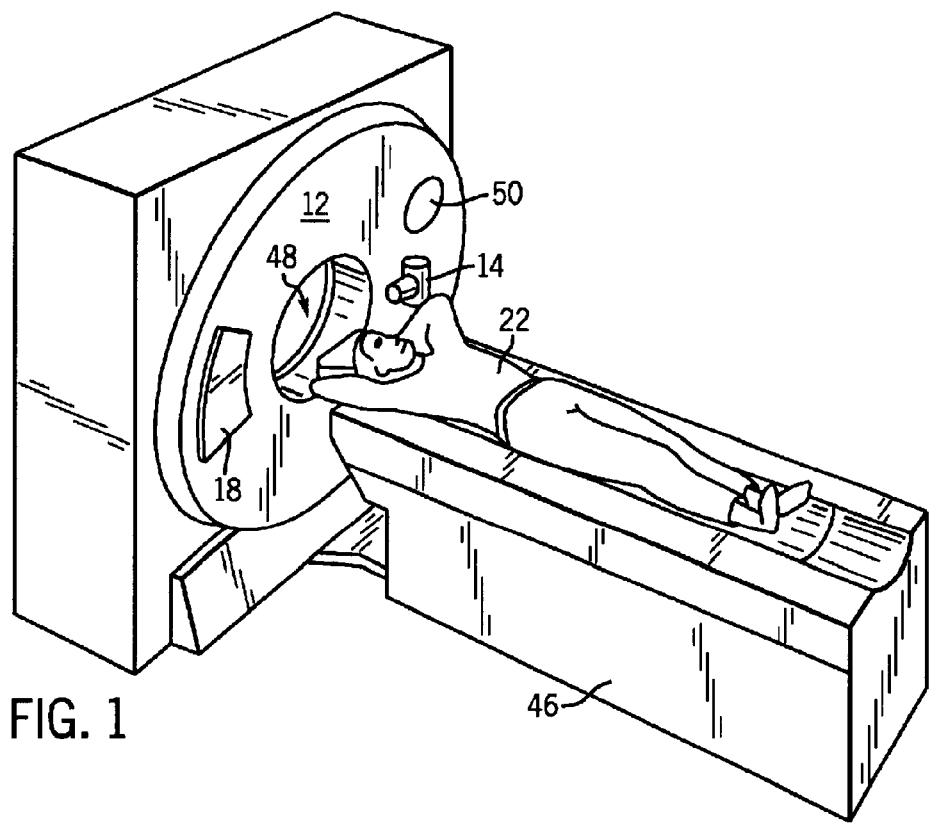
FIG. 1 is a perspective view of a CT imaging system.
Figure 2:
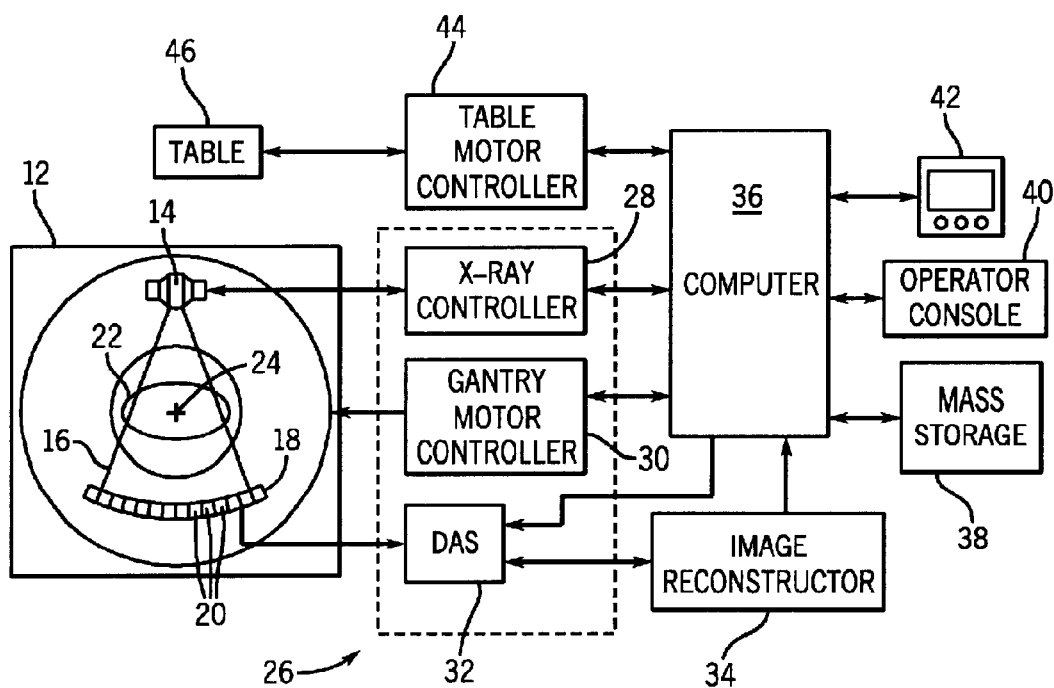
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24. Gantry 12 also includes a gantry control panel 50 that will be discussed with particular reference to FIG. 3.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

The present invention overcomes the aforementioned drawbacks by allowing an operator to maintain continued focus on a patient to be scanned and to closely monitor the patient during the injection sequence. Overall scan time is reduced by decreasing the number of times the operator must travel between the operator console and the patient table. Further, the operator's risk to prolonged radiation exposure is also reduced. Ultimately, the present invention allows for better quality patient care, faster scan times and overall increased throughput, reduced repetitive tasks for the operators, reduced risk of x-ray exposure to operators, and, in some circumstances, a minimizing in the need for multiple operators.

Figure 3:
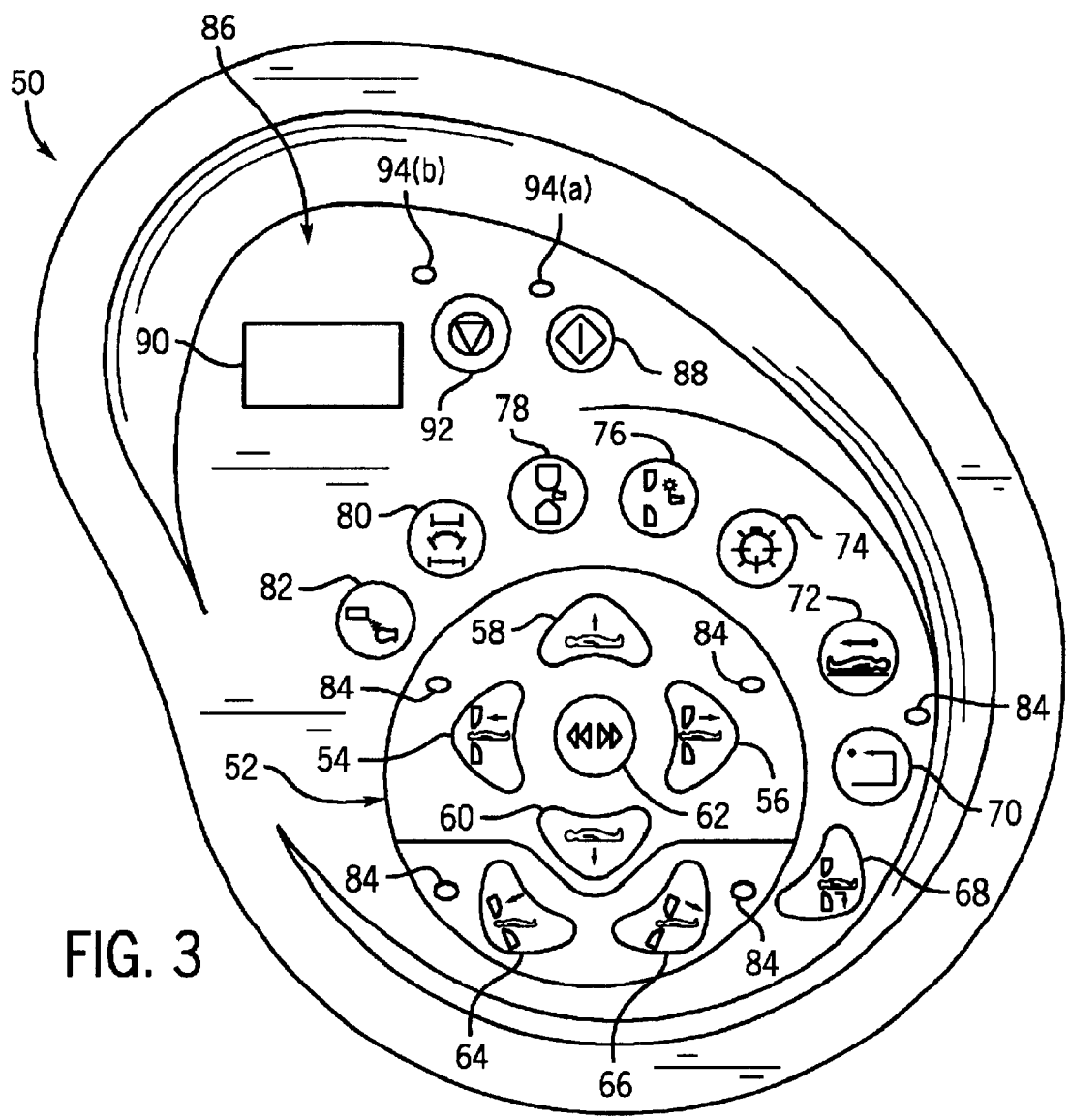
FIG. 3 is a front elevational view of a gantry control panel in accordance with the present invention.

Referring to FIG. 3, an exemplary gantry control panel is shown in accordance with the present invention. Gantry control panel 50 located on a surface of gantry 12, FIG. 1, includes a number of patient/patient table positioning controls 52. Controls 52 allow for positioning of the patent and/or patient table depending upon the specific characteristics of the patient and/or needs of the scanning session. Controls 52 include a patient/table IN button 54 for facilitating positioning of the patient/table toward opening 48 of gantry 12, FIG. 1. A patient/table OUT button 56 is also provided for moving the patient/table out of the gantry opening. To facilitate movement of the patient/table upward and downward, gantry control 50 includes a patient/table Up button 58 and a patient/table DOWN button 60, respectively. Button 62 is provided for facilitating rapid positioning of the patient/table into or out of the gantry opening.

Gantry control panel 50 includes a pair of gantry positioning controls 64 and 66. Control button 64 is used to facilitate tilting of the gantry backward whereas gantry control button 66 is designed to facilitate forward tilting of the gantry. Gantry control panel 50 further includes a patient/table unload-home multiple motions or reset button 68, a reset motion and x-ray power button 70, and a cradle release button 72. Reset button 68 allows an operator to reset the patient table and the gantry to a start position without having to reset the gantry, cradle, and table individually, so that the patient may freely exit the scanner. An alignment lights button 74 is also included for illuminating points on the body of the scanning object so that proper aligning of the scanning object within the scanner be more efficiently and effectively achieved. Landmark setting buttons 76 and 78 are also provided for setting a landmark with internal alignment lights and external alignment lights, respectively. To view tilt and scan range limits, an operator or technologist may depress control button 80. Furthermore, a demonstration of breathing lights for a patient may be displayed by depressing button 82. By providing a demonstration of the breathing lights, the operator can educate the patient on the type of breathing sequence the patient may be asked to follow to satisfy the needs of the scan session. Additionally, gantry control panel 50 includes a number of indicator lights 84 that sequentially illuminate to guide the scanner user to activate control buttons 54–60, 64–70 in the correct sequence.

Gantry control panel 50 further includes a set of scan sequence controls 86. The scan sequence controls 86 allow an operator to initiate an imaging scan and monitor the time between the administering of the contrast agent and the emission of x-rays. That is, the operator may initiate a scan sequence thereby causing injection of the contrast agent by depressing start control button 88. By depressing control button 88, an initial countdown value in terms of seconds appears in countdown display 90. The initial countdown value depends upon the monitoring system and the parameters of the particular scanning session. An initial countdown value may be between 20–40 seconds for a CT system, but may be longer depending upon the scan parameters. Further, other radiation emitting systems may employ a longer delay. However, in one preferred embodiment, countdown display 90 is configured to display up to three digits, therefore, initial countdown values ranging from 100 seconds to 999 seconds are available. Further, a stop scan control button 92 is provided that enables the operator to terminate the scan sequence. That is, if the operator elects to stop the scanning session, the operator may depress button 92 so that the scanning process ceases whereby the countdown display 90 is reset to an initial value.

In a further embodiment, the present invention contemplates the pausing of the scanning process sequence. To facilitate the pausing feature of the present invention, the user may depress STOP button 92 once whereas depressing STOP button 92 a second time causes complete stopping of the scanning process and resetting of the countdown display 90 as was previously discussed. Other methods of facilitating a stop/pause feature using a single button are contemplated and well within the scope of the present invention. That is, a quick depressing of button 92 may signal a pause whereas a lengthy depressing of button 92 may signal a request to completely terminate the scan sequence. A pair of LED lights 94 is provided to indicate to the user which mode is active. That is, illumination of light 94(*a*) indicates that the start scan process has been initiated and is actively counting down to a final value of zero whereas illumination of LED light 94(*b*) indicates that the scanning process has been either paused or terminated.

Figure 4:
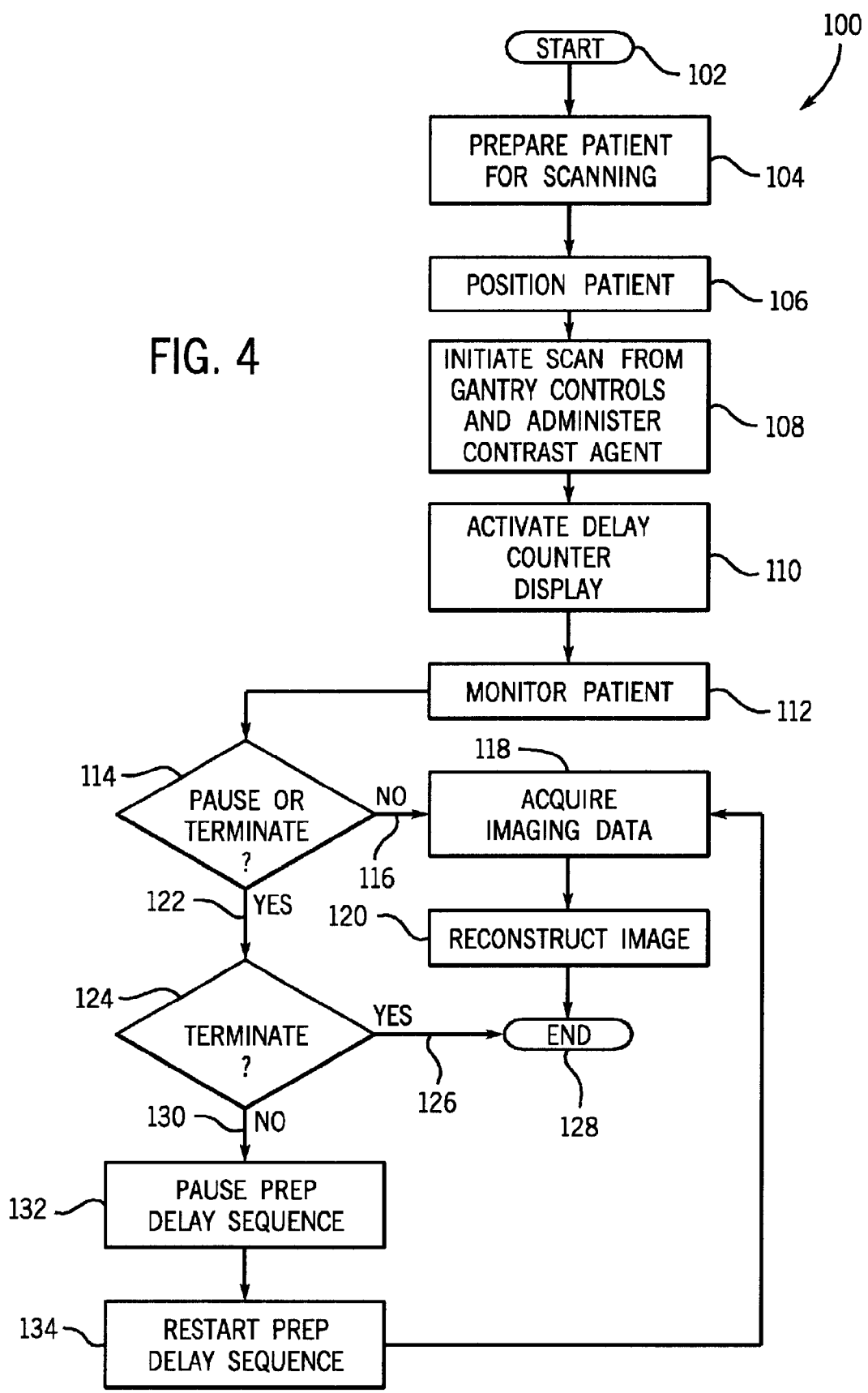
FIG. 4 is a flow chart illustrating the steps of an imaging technique in accordance with the present invention.

Referring to FIG. 4, a method 100 of imaging a patient in accordance with the present invention begins at 102 with preparing the patient for scanning at 104. Preparing the patient for scanning may include a number of tasks such as connecting an IV to the patient for subsequent injection of a contrast agent. The patient is then positioned within the scanner at 106. After the patient is properly prepared 104 and properly positioned 106, a contrast agent is administered at 108 by activation of a start scan control of a set of gantry controls. The contrast agent will be used to concentrate the imaging data acquisition to a particular anatomical region of the patient. As indicated previously, there is typically a 20–40 second delay between administering of the contrast agent 108 and an onset of x-ray emission. Therefore, at 110, a prep delay counter is initiated so that the 20–40 second time period may be sufficiently monitored.

After the sequence is initiated at 108 and the counter is activated at 110, the patient is monitored to determine any adverse reactions to the injected contrast agent at 112. Based on the patient's reaction to the contrast agent or other concerns regarding proper scanning parameters, the scanning process may be paused or terminated. Therefore, the present invention contemplates at 114 the pausing or terminating of the scanning process. If the scanning process is not to be paused or terminated 114, 116, x-rays are emitted and imaging data are acquired at 118 for subsequent image reconstruction at 120. Because the scan sequence is initiated from a set of gantry controls rather than a separate operating console positioned in a room separate from the room housing the scanner, the present invention contemplates the operator maintaining a continual presence with the patient even during the emission of x-rays and acquisition of data. To reduce the risk of radiation exposure however, it is imperative that the operator wear proper protective attire sufficient to block the penetration of x-rays.

However, the operator may elect to leave the patient's side and exit the room housing the scanner during the emission of x-rays and acquisition of imaging data to further reduce the risk of radiation exposure. Maintaining a presence next to the patient during x-ray emission and data acquisition wearing protective lead-lined attire may be necessary at times however to attend to special patients such as small children or those with physical disabilities.

Still referring to FIG. 4, if the scan sequence is to be paused or terminated 114, 122, the operator must determine at 124 whether to terminate the scan sequence. If the operator elects to terminate the scan sequence 124, 126, the scanning session is likewise terminated at 128 whereupon method 100 concludes. However, if the operator elects to not terminate the scan sequence but rather simply pause the scan sequence 124, 130, the scanning session is paused at 132 so that the operator may attend to those needs and/or concerns that warranted pausing of the scanning process. Once those concerns are properly addressed at 132, the scam sequence is restarted at 134 for subsequent data acquisition at 118 and image reconstruction at 120.

Therefore, in accordance with one embodiment of the present invention, a gantry control panel for use with a radiation emitting medical imaging scanner is provided. The gantry control panel includes a scan sequence initiator control and a scan sequence terminator control. Further, the gantry control panel is located on a gantry of the radiation emitting medical imaging scanner and is further configured to be non-remotely located from a patient table.

In accordance with another embodiment of the present invention, a gantry for use with a radiation emitting medical imaging scanner includes a radiation emitting source, a radiation detector, and an opening for receiving a subject therethrough. The gantry further includes at least one faceplate wherein the at least one faceplate has a first set of controls and a second set of controls. Additionally, one of the first set and the second set of controls is configured to at least initiate a scan sequence.

In accordance with yet another embodiment of the present invention, a CT system comprising a radiation projection source, a radiation detector, and a light detector coupled to the radiation detector. A data acquisition system is also provided and is electrically connected to the light detector. The CT system further includes a rotatable gantry positioned about a subject table and having an opening to receive a subject to be scanned therethrough. The gantry includes a set of scanning controls located immediately adjacent the rotatable gantry such that an operator may utilize the controls while near the subject.

In accordance with another embodiment of the present invention, a set of gantry controls includes a means for positioning a subject within an imaging space and a means for initiating a scan sequence from an area immediately adjacent the subject. A means for acquiring imaging data is also provided.

In accordance with yet another embodiment of the present invention, a method of imaging a subject includes preparing a subject for scanning and positioning the subject within an imaging space. The method further includes initiating a scan process from a set of controls positioned on a side of a gantry and monitoring the subject non-remotely from the set of controls and the subject. The method also includes the step of acquiring imaging data.

The present invention has been described with respect to a CT imaging system. However, the present invention is applicable with x-ray imaging systems as well as any other radiation-based scanner.

The present invention has been described in terms of the preferred embodiment, and it is recognized that equivalents, alternatives, and modifications, aside from those expressly stated, are possible and within the scope of the appending claims.

What is claimed is:

1. A gantry control panel for use with a radiation emitting medical imaging scanner, the control panel comprising:
 a set of patient table positioning controls configured to facilitate positioning of a patient for imaging;
 a scan sequence initiator control;
 a scan sequence terminator control;
 a timer control configured to detect activation of the scan sequence initiator control and determine a time between the activation and initiation of the scan sequence;
 a counter control configured to count down the time and display the countdown on a scan time counter display; and wherein the gantry control panel is located on a gantry of the radiation emitting medical imaging scanner non-remotely from a patient table.

2. The gantry control panel of claim 1 further comprising a pair of status indicator lights wherein one indicator light indicates activation of the scan sequence initiator control and the other indicator light indicates activation of the scan sequence terminator control.

3. The gantry control panel of claim 1 further comprising a set of patient table positioning controls configured to facilitate positioning of a patient for imaging and a scan time counter display.

4. The gantry control panel of claim 3 wherein the scan time counter display is configured to display three digits.

5. The gantry control panel of claim 3 wherein the scan time counter display is configured to increment descendingly from an initial value toward a final value.

6. The gantry control panel of claim 5 wherein the final value is zero and wherein the initial value is indicative of time between initiation of a scan sequence and an onset of high frequency electromagnetic energy emission toward an imaging subject to be scanned.

7. The gantry control panel of claim 1 wherein the scan sequence initiator control and the scan sequence terminator control are accessible from an area immediately adjacent to the patient table.

8. The gantry control panel of claim 1 wherein the scan sequence terminator control includes a scan sequence pauser control.

9. A gantry for use with a radiation emitting medical imaging scanner, the gantry comprising:
a radiation emitting source;
a radiation detector;
an opening for receiving a subject therethrough;
at least one faceplate, the at least one faceplate having a first set of controls and a second set of controls; and
wherein one of the first set and the second set of controls is configured to detect injection of a contrast agent, determine a time between the injection and data acquisition, count down the time, and display the time on a scan counter display.

10. The gantry of claim 9 wherein the at least one faceplate has a generally circular shape.

11. The gantry of claim 10 wherein the at least one faceplate has a pear shape.

12. The gantry of claim 9 wherein the other one of the first set and the second set of controls includes a subset of controls, wherein the subset of controls includes a plurality of table positioning controls.

13. The gantry of claim 12 wherein the other one of the first set and the second set of controls includes an array of controls, the array of controls being positioned along an outer periphery of the subset of controls.

14. The gantry of claim 13 wherein each control of the array is circular-shaped and wherein a number of the controls of the subset are bean-shaped.

15. The gantry of claim 12 wherein the plurality of table positioning controls are diamondly arranged and wherein the arrangement of the plurality of table positioning controls defines an inner region having a rapid table movement control therein.

16. The gantry of claim 12 wherein the subset of controls includes a pair of gantry positioning controls.

17. The gantry of claim 9 wherein the one of the first set and the second set of controls is located along an outer periphery of the other one of the first set and the second set of controls.

18. The gantry of claim 17 wherein the one of the first set and the second set of controls is located above the other one of the first set and the second set of controls.

19. The gantry of claim 18 wherein the one of the first set and the second set of controls includes:
a start scan sequence control; and
a stop scan sequence control.

20. The gantry of claim 19 wherein the start scan sequence control is configured to administer a contrast agent to the subject upon activation thereof.

21. The gantry of claim 19 wherein the counter display is configured to display up to three digits and wherein the counter display is rectangular-shaped and positioned adjacent to the start scan sequence control.

22. A CT system comprising:
a radiation projection source;
a radiation detector;
a light detector coupled to the radiation detector;
a data acquisition system electrically connected to the light detector; and
a rotatable gantry positioned about a subject table and having an opening to receive a subject to be scanned therethrough, the gantry including:
a set of scanning controls located immediately adjacent the rotatable gantry such that an operator may utilize the controls while near the subject; and
a number of breathing lights viewable by the subject and controllable by the operator such the operator can selectively illuminate the number of breathing lights to provide a preferable breathing sequence to the subject.

23. The CT system of claim 22 further comprising a set of patient table positioning controls and wherein the set of scanning controls includes a start scan control and a stop scan control.

24. The CT system of claim 23 wherein the stop scan control is configured to stop and pause a scan sequence.

25. The CT system of claim 23 further comprising a plurality of indicator lights wherein the start scan control and the scan control each has a corresponding indicator light.

26. The CT system of claim 23 further comprising:
a second set of patient table positioning controls;
a second start scan control; and
a second stop scan control.

27. The CT system of claim 26 wherein the set of patient table positioning controls, the start scan control, and the stop scan control are positioned on a side of the gantry and the second set of patient table positioning controls, the second start scan control, and the second stop scan control are positioned on an opposite side of the gantry.

28. A set of gantry controls comprising:
means for positioning a subject within an imaging space;
means for initiating a scan sequence from an area immediately adjacent the subject; and
means for displaying a real-time status of data acquisition relative to an injection of contrast agent such that an operator may cease non-remote monitoring of the patient before acquisition of imaging data.

29. The set of gantry controls of claim 28 further comprising:
means for pausing the scan sequence; and
means for terminating the scan sequence.

30. The set of gantry controls of claim 28 wherein means for initiating a scan sequence includes means for administering a contrast agent to a subject to be scanned.

31. A method of imaging a subject, the method comprising:
  preparing a subject for scanning;
  positioning the subject within an imaging space;
  initiating a scan process from a set of controls positioned on a side of a gantry;
  monitoring the subject non-remotely from the set of controls and the subject to determine a subject's reaction to a contrast agent;
  determining a time until x-ray emission from a counter display on the gantry; and
  ceasing non-remote monitoring of the subject before the time expires.

32. The method of claim 31 further comprising pausing the scan process from the set of controls.

33. The method of claim 31 further comprising terminating the scan process from the set of controls.

34. The method of claim 31 further comprising avoiding exposure to radiation during the acquisition of imaging data.

35. The method of claim 31 further comprising including a count down timer and display with the set of controls.

* * * * *